United States Patent [19]
Stearns et al.

[11] Patent Number: 5,594,346
[45] Date of Patent: Jan. 14, 1997

[54] APPARATUS AND METHODS FOR IDENTIFYING AND QUANTIFYING COMPOUNDS USING A PLURALITY OF PULSED RARE GAS PHOTOIONIZATION DETECTORS

[75] Inventors: Stanley D. Stearns, Houston; Wayne E. Wentworth, Pearland, both of Tex.

[73] Assignee: Valco Instruments Co., Inc., Houston, Tex.

[21] Appl. No.: 349,046

[22] Filed: Dec. 2, 1994

Related U.S. Application Data

[63] Continuation-in-part of Ser. No. 662,149, Feb. 28, 1991, Pat. No. 5,153,519, Ser. No. 956,632, Oct. 5, 1992, Pat. No. 5,317,271, Ser. No. 176,968, Jan. 3, 1994, Pat. No. 5,394,092, Ser. No. 201,467, Feb. 25, 1994, Pat. No. 5,394,090, and Ser. No. 201,469, Feb. 25, 1994, Pat. No. 5,394,091.

[51] Int. Cl.⁶ .......................... G01N 27/62; G01N 27/68
[52] U.S. Cl. .......................... 324/464; 324/455; 73/28.02
[58] Field of Search .................... 324/449, 450, 324/452, 455, 464, 123 R, 71.4; 73/28.02; 250/379, 385; 313/231.41, 231.71; 315/111.01, 111.91; 436/153

[56] References Cited

U.S. PATENT DOCUMENTS

| | | | |
|---|---|---|---|
| 3,540,851 | 11/1970 | Vree et al. | 324/464 X |
| 3,679,973 | 7/1972 | Smith, Jr. et al. | 324/464 X |
| 4,724,394 | 2/1988 | Langer et al. | 324/464 |
| 4,851,683 | 7/1989 | Yang et al. | 250/339 |
| 5,153,519 | 10/1992 | Wentworth et al. | 324/464 |
| 5,317,271 | 5/1994 | Wentworth et al. | 324/464 |
| 5,338,931 | 8/1994 | Spangler et al. | 250/287 |
| 5,394,090 | 2/1995 | Wentworth et al. | 324/464 |
| 5,394,091 | 2/1995 | Wentworth et al. | 324/464 |
| 5,394,092 | 2/1995 | Wentworth et al. | 324/464 |

OTHER PUBLICATIONS

A Compilation of Research on Pulsed Discharge Detectors, Article, Summary of Paper Presented at the Pittsburgh Conference, 1994.

Introduction to: Pulsed Discharge Helium Ionization Detector, Reprint of Publication in the Journal of Chromatographia, vol. 34, No. 5–8, pp. 219–115 (1992).

Introduction to: Pulsed Discharge Electron Capture Detector Reprint devoted solely to the PDECD (J of Chromatogra. Sci., vol. 30, pp. 478–485, (1992).

Pulsed Discharge Helium Ionization Detector, W. E. Wentworth, S. V. Vasnin, Stearns, & Meyer, Chromatographia, vol. 34, No. 5–8, Sep./Oct. 1992.

Pulsed Discharge Photoionization Detector (PDPID), A Summary of a paper presented at the 1994—Pittsburgh Conference by W. E. Wentworth.

(List continued on next page.)

*Primary Examiner*—Kenneth A. Wieder
*Assistant Examiner*—Diep Do
*Attorney, Agent, or Firm*—Donald Gunn

[57] ABSTRACT

A pulsed discharge photoinoization detector is set forth which comprises a plurality of closed chambers for receiving different types of carrier gas flowing there through between inlets and outlets. The carrier gases are exposed to a pair of electrodes forming a spark across each chamber and through each carrier gas. At least one component of each type of carrier gas is excited within each chamber by the spark discharges, and the resonance energies of each type of carrier gas are different. The sample to be analyzed is split and a portion is injected into each of the closed chambers where it is exposed to the excited carrier gases. Carrier gases, upon decay, serve as sources of ionizing radiation of differing energy which react with compounds within the sample gas producing ionization currents which are a function of the types of sample gas compounds and the types of carrier gases. Ionization currents are measured in each detector chamber simultaneously and are used to uniquely identify unknown compounds within the sample gas.

23 Claims, 3 Drawing Sheets

OTHER PUBLICATIONS

Pulsed Discharge Emission Detector–Application to Analytical Spectroscopy of Permanent Gases, Vasnin, Wentworth, Stearns & Meyer, Chromatographia, vol. 34, No. 5–8, Sep./Oct. 1992.

Pulsed Discharge Helium Ionization Detector, A Universal Detector for Inorganic and Organic Compounds at the Subpicogram Level, Wentworth, et al, Version of 5/25.

Reprinted from Process Control & Quality, 5 (1993) 193–204, Elsevier Science B.V., Amsterdam, Pulsed–Discharge Helium Ionization/Electron Capture/Emission Detector of Chlorinated Compounds, Wentworth, et al.

Environmental Applications of the Pulsed–Discharge Electron–Capture Detector, Wentworth, D'Sa & Cai, Journal of Chromatographic Science, vol. 30, Dec. 1992.

Introduction to: Pulsed Discharge Emission Detector (PDED) Chromatographia, vol. 34, pp. 226–234, (1992).

APPARATUS AND METHODS FOR IDENTIFYING AND QUANTIFYING COMPOUNDS USING A PLURALITY OF PULSED RARE GAS PHOTOIONIZATION DETECTORS

This disclosure is a continuation in part of application Ser. No. 662,149 which was filed on Feb. 28, 1991 and which issued as U.S. Pat. No. 5,153,519 on Oct. 6, 1992, also application Ser. No. 956,632 which was filed on Oct. 5, 1992, now issued as U.S. Pat. No. 5,317,271 on May 31, 1994, application Ser. No. 176,968 which was filed on Jan. 3, 1994, now U.S. Pat. No. 4,394,092 and also application Ser. No. 201,467, now U.S. Pat. No. 5,394,090 and application Ser. No. 201,469, now U.S. Pat. No. 5,394,091, both filed Feb. 25, 1994.

BACKGROUND OF THE DISCLOSURE

The present disclosure involves the qualitative analysis of gases for compounds of interest and is an extension of the apparatus and methods taught in U.S. Pat. No. 5,153,519.

The referenced patent discloses the creation of several charged species by a pulsed direct current (DC) spark discharge acting on a carrier gas containing other compounds to be identified and quantified. The carrier gas is preferably an inert gas and is typically helium. The charged species are used to classify and/or quantify the unknown compounds in the carrier. This detector is connected with upstream or downstream devices such as a sample source, gas chromatograph (GC) column, spectrum analyzer or the like. A sample to be analyzed is loaded for flow along with the carrier gas into a system chamber. While the sample passes through the detection device, a pulsed, high voltage DC spark discharges to form selected charged or energized species within the gas. The spark discharge simultaneously initiates several types of detection systems. For instance, the very short DC spark creates a readily available thermalized electron flux which can be used in a detection system. In an alternate mode of operation, the spark creates a more slowly diffused flux of metastable helium atoms which drift toward selected electrodes within the detector at a controlled rate. The helium atoms will react with molecules of the sample to surrender the excess energy from the excited state to cause sample molecule ionization which, as a secondary and delayed reaction, can be measured by a detection system. Another aspect involves photoionization of gas into positive and negative charged particles normally recombining at high speed. If a select sweep pulse voltage is applied, the recombination is prevented to furnish a signal indicative of the unknown compounds within the gas mixture. Identification and quantification of compounds of interest can, to some extent, be controlled by varying the timing of the spark, the electrode geometry, the voltages of the detector segments, and the modes of interactions observed within the plasma. A complete discussion of the apparatus and basic principles of the measurements are disclosed in detail in U.S. Pat. No. 5,153,519 and are entered herewithin by reference.

There are several limitations to the means and methods disclosed in U.S. Pat. No. 5,153,519. As a first example, the technique provides little control of the compounds within the carrier gas and sample gas mixture which are ionized and therefore detected. If, as an example, it is desired to measure a trace impurity compound in air and both the trace compound and the major constituents of air all are ionized, the relative magnitudes of the major air constituents will introduce serious signal to noise problems thereby degrading the measurement of the desired trace impurity. The teachings disclosed in previously referenced application Ser. No. 08/176,968 present means for not ionizing the major constituents of air, but at the expense of not ionizing, and therefore not detecting, some classes of compounds which may be of interest. In addition, the apparatus disclosed in several of the previously referenced devices are constructed such that the chamber electrodes are exposed to a mixture of carrier and the compound to be detected. Often the compounds of interest are corrosive resulting in corrosion of the discharge electrodes thereby affecting the operation of the measuring system as a function of time. The previously referenced Ser. No. 08/349,039 overcomes some of the aforementioned shortcomings of the cited reference devices. First, the sample gas is not passed through the discharge electrodes thereby minimizing corrosion of the electrodes. Second, selective ionization of trace compounds within the sample is accomplished by selecting the dopant of the carrier gas. This, however, requires prior knowledge of the major constituents of the sample gas and the ionization potential of the trace compound to be measured within the sample gas. As an example, it might be of interest to monitor commercially produced nitrogen dioxide ($NO_2$) for a trace impurity such as boron triflouride ($BF_3$). Helium doped with xenon is an ideal carrier gas to measure in that the ionization potential of $BF_3$ is below the resonance of xenon while the ionization potential of $NO_2$ is above the resonance energy of xenon. Any $BF_3$ impurity is, therefore, selectively ionized while the major constituent $NO_2$ is not ionized. The targeted impurity can be measured with the signal to noise being maximized using the teachings of the cited application assuming that the aforementioned characteristics of the sample gas are known. The dopant can not, however, be effectively selected if unless the type of compound to be detected is known.

SUMMARY OF THE INVENTION

The present invention is directed toward methods and apparatus for identifying and quantifying unknown compounds within a sample gas using selective ionization techniques. A plurality of detection devices or "detectors" of the type described in the previously referenced U.S. Pat. No. 5,153,519 and copending applications are used to simultaneously analyze a sample gas. Carrier gas is passed through the detector and a high voltage DC spark discharges to form selectively charged or energized species within the gas. The sample gas is "split" and likewise passes through each detector and is commingled with the excited carrier gas. The use of the detector disclosed in application Ser. No. 08/349, 039 is preferred in the current invention in that the sample gas does not pass through the spark discharge and therefore minimizes the corrosion of the discharge electrodes. The operation of the detector will be detailed in a following section. Sample gas is input simultaneously into each detector as will likewise be described in detail in a following section.

Selective ionization within a given detector is controlled by the selection of carrier gas. The carrier gas of the first detector is preferably helium (He). The helium is excited by the spark discharge creating a flux of metastable helium which drifts downstream from the spark gap. Sample gas split is input into the detector downstream from the spark discharge and is exposed to the excited helium. Photons are emitted from the essentially continuum $He_2$ spectrum from 70 to 92 nm with energies ranging from 13.5 to 17.7 eV. The decay of helium, in turn, ionizes compounds within the sample gas with ionization potentials lower than 17.7 eV.

Ionization current indicative of sample gas ionization is measured. The second detector might utilize a carrier gas of helium doped with argon (Ar). Again, helium is excited by the spark discharge creating metastables which are commingled with the Ar dopant in the vicinity of the spark gap. The split of sample gas is again exposed to the mixture of excited helium doped with Ar within the detector chamber. In this case, the decay of excited helium also excites the dopant gas Ar by a time delayed reaction. Photons are emitted from the well known resonance lines of argon at 104.8 and 106.6 nm which have energies of 11.83 eV and 11.62 eV, respectively. These emissions, in turn, ionize any compounds within the sample gas with ionization potentials lower than 11.83 eV. Ionization current indicative of sample gas ionization within this detector is measured. Although the sample gas splits which are passed though the first and second ionization detectors are identical, the respective ionization currents will be different because of emissions and subsequent ionizations by the argon dopant. A third detector might utilize a carrier gas of helium doped with krypton (Kr). Once again, helium is excited by the spark discharge creating metastables which are commingled with the Kr dopant in the vicinity of the spark gap. The split of sample gas is once again exposed to the mixture of excited helium and Kr dopant within the detector chamber. In this case, the decay of helium excites the Kr dopant gas by a time delayed reaction. Photons are emitted from the excited Kr with a maximum energy of 10.1 eV. These emissions, in turn, ionize any compounds within the sample gas split with ionization potentials lower than 10.1 eV. Ionization current indicative of sample gas ionization within this detector is also measured. Once again, the ionization current from the third detector using Kr doped helium will differ from the ionization currents measured with the first two detectors although the sample gas splits are identical. This is again due to the unique emissions of the dopant which is, in this case, Kr. The relationships of measured ionization currents are a function of the types of compounds within the sample gas. The magnitudes of the measured currents are a function of the concentrations of the compounds within the sample gas. Stated another way, each type of compound exhibits a "signature" of relative ionization currents.

Any number of detectors can be used to simultaneously measure ionization currents from splits of sample gas as described in the previous paragraph. A fourth detector may comprise a carrier gas of xenon (Xe) doped helium wherein excited Xe emits photons with a maximum energy of approximately 8.5 eV. As a general rule, the precision to which unknown compounds can be identified within the sample gas increases as the number of detectors with unique carrier gases increases. Analytical methods for identifying compounds within the sample will be presented in following sections. If the source of sample gas is the output of a gas chromatographic (GC) column, the observed retention times of the eluted peaks can be used to narrow the unknown sample compounds to perhaps ten or twelve possibilities per eluted peak. The analysis of each eluted peak with the present invention then yields very precise identification of the unknown compounds using perhaps three to five detectors, each with a different carrier gas.

Currents measured with each detector are input into a computing means in which the identity and concentrations of compounds within the sample gas are determined using predetermined identity and calibration relationships.

BRIEF DESCRIPTION OF THE DRAWINGS

So that the manner in which the above recited features, advantages and objectives of the present invention are attained and can be understood in detail, more particular description of the invention, briefly summarized above, may be had by reference to the embodiments thereof which are illustrated in the appended drawings. It is to be noted, however, that the appended drawings illustrate only typical embodiments of the invention and are therefore not to be considered limiting of its scope, for the invention may admit to other equally effective embodiments.

DETAILED DESCRIPTION OF THE PREFERRED EMBODIMENT

The present disclosure is directed to an ionization detector system used to identify compounds and determine the concentrations of compounds in a gas sample. The system is connected upstream or downstream with existing equipment. The cooperative equipment constitutes one context for ease of explanation. This detector system is devoid of radioactive sources and hence can be used where radioactive materials are limited. Heretofore, it has been common to operate electron capture devices with radioactive material such as a source of ionizing radiation, the most common being tritium and nickel-63. The system yields accurate and precise results even though the sample may contain many types of unknown compounds. The system is physically rugged, relatively small in size, and requires minimal maintenance.

Figure 1:
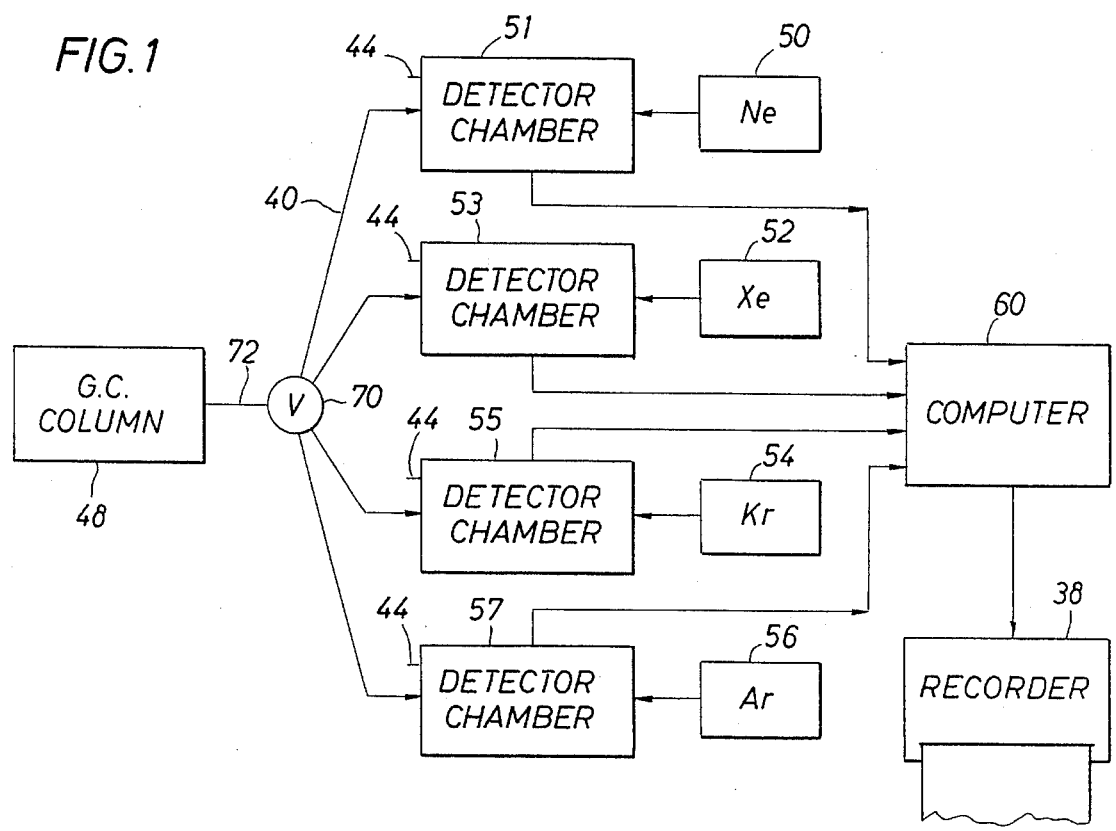
FIG. 1 illustrates in block diagram format the major elements of the invention and the functional cooperation between these major elements.

Attention is first directed to FIG. 1 which depicts the overall detection system in block diagram form. As discussed previously, the system comprised a plurality of ionization detectors, with four such detector chambers denoted by the numerals 51, 53, 55 and 57 being used for purposes of illustration. The source of sample gas is shown as a gas chromatograph (GC) column 48. The flow from the GC 48 is directed through conduit 72 to a fitting 70 which portions or "splits" the flow into four equal parts which are directed by flow conduits 40 to four ionization detector chambers denoted as 51, 53, 55 and 57. Four different carrier gas mixtures from sources 50, 52, 54 and 56 flow into detector chambers 51, 53, 55 and 57, respectively. The carrier gas constituents are excited and commingled with the sample gas splits within each chamber. The excited carrier gases ionize components of the sample gas thereby generating an ionization current. Mixtures of carrier and sample gas are vented from each chamber through a port 44. Measures of ionization current generated within chambers 51, 53, 55 and 57 are transferred to the computer 60 by means of electrical conductors 70, 72, 74 and 76. The measures of current are processed within the computer 60 to obtain the identity and concentrations of compounds within the sample gas. Results are output from the computer to a suitable recording means denoted by the numeral 38. It is again emphasized that the number of detectors can be varied. FIG. 1 illustrates the use of four detectors. The use of only three detectors will be illustrated in subsequent sections of this disclosure. In analyzing sample gas which can contain a large number of different unknown compounds, accuracy and precision may be maximized by using six or eight or even more detectors.

Attention is now directed to a more detailed illustration of the type of ionization detector used in the preferred embodiment as well as details of the operation of the detector. It should be understood that other types of ionization detectors can be used and still fall within the scope of the current invention.

Figure 2:
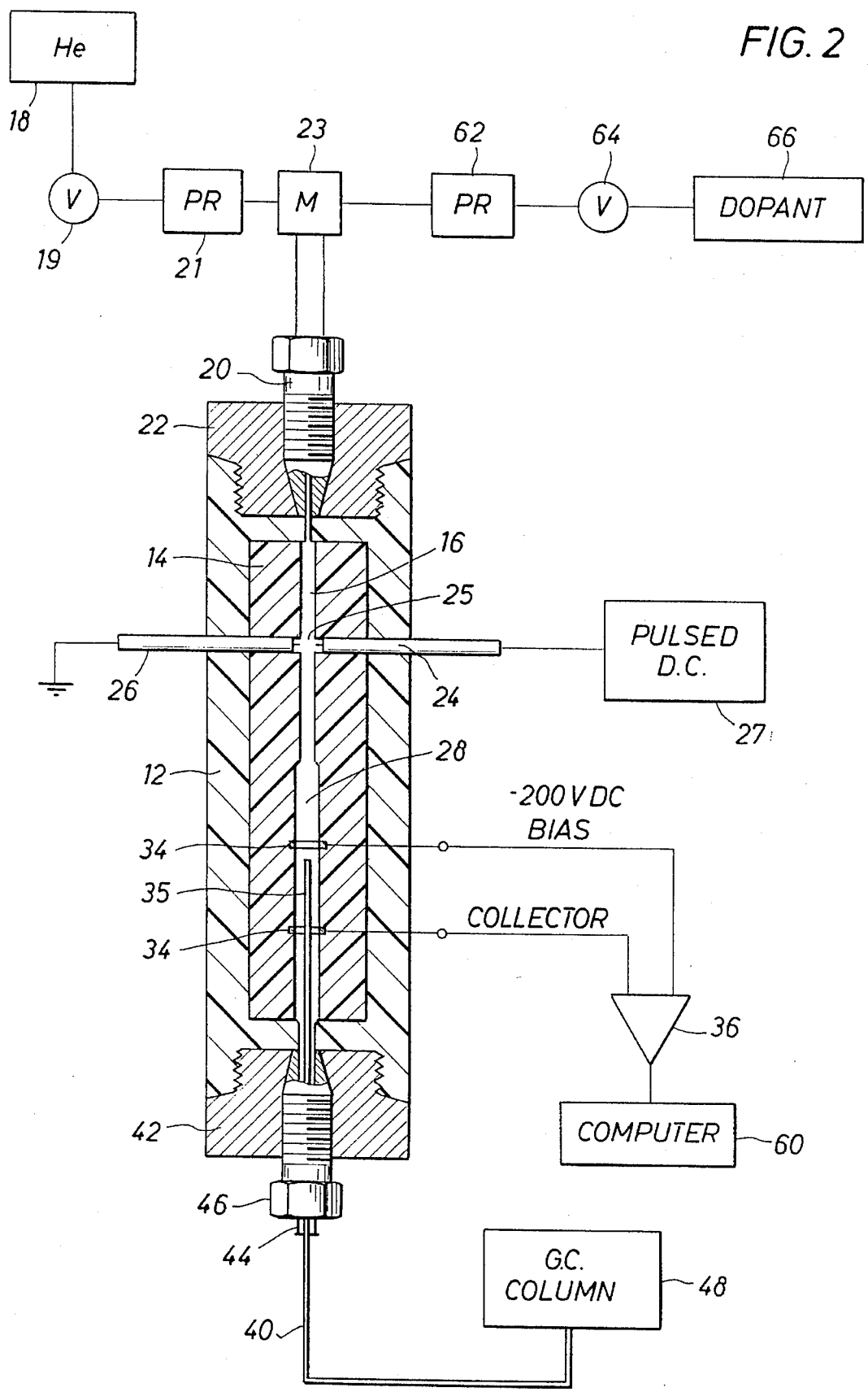
FIG. 2 illustrates detail of an ionization detector.

Referring to FIG. 2, the numeral 10 identifies the detector system of the present invention which will be referred to specifically as the pulsed discharge photoionization capture detector or PDPID. It is constructed with a long cylindrical housing 12 which contains a cylindrical member 14 which is axially hollow at 16. This forms a passage through which a carrier gas is introduced. The preferred carrier gas is helium although other inert gas such as Ar or Kr doped helium can be used. The helium flows from a source 18 through a valve 19 and a regulator 21 to deliver helium at a pressure slightly above atmospheric pressure and flowing at a rate of about 20 to about 150 milliliters per minute. The helium flow is directed to the manifold 23 which is attached to an industry standard fitting 20 formed in a fitting body 22 at the first end of the body 12 of the PDPID. By means of a suitable externally threaded nut, the fitting body 22 is held in the illustrated position to assure locking in the PDPID apparatus 10. As mentioned in earlier discussion, the carrier can comprise a dopant in one or more detectors. The detector illustrated in FIG. 2 does provide means for adding dopant gas. The reservoir for the dopant gas is identified by the numeral 66. This reservoir is connected through valve 64 and pressure regulator 62 to the manifold 23. By opening valves 19 and valve 64, helium and the dopant gas are introduced at the manifold 23 and flow directly into the axial passage 16 and move between the space electrodes 24 and 26.

The electrodes 24 and 26 preferably terminate in facing end faces. More specifically, the facing end faces are constructed on metal rods having a diameter of about 1/16" and which are spaced with end faces approximately 1/16" across passage 16. The faces of the electrodes are preferably flush with the wall of the passage 16. In an optional embodiment, the electrodes are reduced in diameter to a smaller diameter of about 0.3 mm. This can be obtained by forming the two electrodes 24 and 26 of wire stock of that size. In an alternate aspect, larger electrodes can be used and sharpened points can be located so that the spark is traversed to the gas flow in the passage 16. The electrodes 24 and 26 are supported in the cylindrical member 14 which is made of electrically insulating material such as plastic or glass. The terminals of electrodes 24 and 26 are likewise electrically insulated from the body 12 of the PDPID which may be made of electrically conducting material such as stainless steel. The electrode 26 is grounded. The electrode 24 is provided with a high voltage pulse of short time duration by the DC source 27 as described in detail in previously referenced U.S. Pat. No. 5,153,519. The two terminals 24 and 26 which form the spark define a sharply fixed, narrowly constrained spark on each spark formation so that the spark does not dance around the two electrode faces, and remains in the form of a straight line. Consequently, it is not necessary to otherwise confine the spark location.

Figure 3:
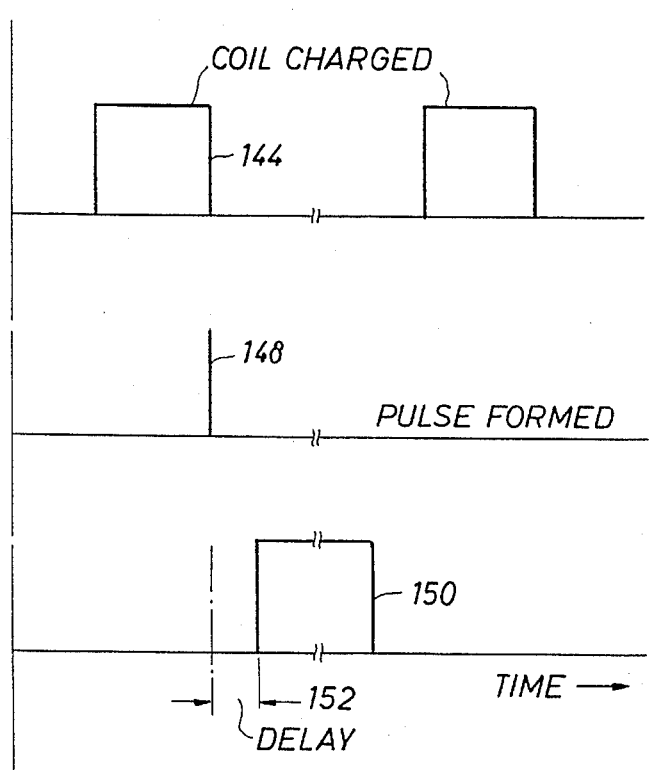
FIG. 3 depicts various timing parameters used in pulsing the spark discharge of the ionization detectors.

FIG. 3 of the drawings depicts several curves which are shown as a function of time. The top curve shows the charging current in the pulse 144 which forms the necessary charge for the operation of the high voltage discharge circuit 143. That circuit forms an output 148 which is a discharge pulse of relatively short duration in time. There is a detection interval which is delayed by a specified time 152, and then a detection pulse is formed at 150.

The flow passage 16 connects downstream with a larger axial hollow passage 28 within cylindrical member 14. Conducting rings 34 and 35 are positioned axially along cylindrical member 14 and are exposed to passage 28. Ring 34 serves as a bias electrode with a bias voltage and also serves as a first terminal for the electrometer 36. The bias can range from about −50 VDC to −400 VDC; bias variation is a scale factor. A bias of −200 VDC is depicted in the drawing of FIG. 2 for purposes of illustration. The second ring 35 is allowed to float and serves as the second terminal for the electrometer 36. The electrometer 36 measures current resulting from the ionization of the trace compounds by the excited carrier gas. The electrometer is input to computer 60 which, when combined with inputs from other detectors, yields the types and concentrations of compounds within the sample gas.

The sample gas is input into the passage 28 of the PDPID by way of the capillary or injection tube 40. In the preferred embodiment, sample gas is supplied at a constant flow rate from the gas chromatograph (GC) column 48. The injector tube 40 is preferably coaxially centered within the exhaust or exit passage 44. The exit passage 44 connects with passage 28 through a standard fitting body 42 which, in turn, defines and seals the second end of the body 12 of the PDPID.

Carrier gas which is introduced into the PDPID system flows from top to bottom through the chamber as illustrated in FIG. 2. Sample gas from the GC column 48 enters the passage 28 through the injector tube 40. In this region, the sample gas and the carrier gas excited by the spark discharge commingle. Compounds within the sample gas are ionized as will be detailed in the following section thereby producing a response of the electrometer 36 which is indicative of the type and concentration of the compounds of interest. The carrier gas flow is substantially greater than the sample gas flow from the injector tube 40. After a brief period of commingling and reacting, the mixture of sample and carrier gas is swept from the passage 28 of the PDPID chamber and exhausted through the outlet 44.

Attention is now directed toward reactions which take place within the PDPID device. Carrier gas mixture comprising an inert gas which is preferably helium and a dopant gas flows into the PDPID through inlet fitting 20 and ultimately into the spark gap 25 where ions and atoms in the excited state are formed. As mentioned previously, the preferred major constituent of the carrier gas is helium. If a dopant is not utilized in the particular detector, helium is excited. For purposes of illustration, it will be assumed that dopant is used. In this situation, the dopant component of the carrier gas, designated hereafter as "D", is energized and raised to an excited state. The excited dopant passes from the vicinity of spark gap 25 through passage 16 and into the passage 28 of the PDPID. Dopant D in the excited state emits photons. Using argon as an example dopant, emission arises from the well known resonance lines of argon at 104.8 and 106.6 nm with corresponding energies of 11.83 and 11.62 eV, respectively. By mixing any of the previously specified dopant gases D with the primary carrier gas helium and exciting the carrier gas mixture at the spark gap 25, a source of ionizing radiation, excited dopant (D*), is created along with other components. These other components are detailed in previously referenced U.S. Pat. No. 5,153,519. The carrier gas containing D* decays rapidly within approximately 5 microseconds after excitation. Some of the photons from this decay process pass from the region of the spark gap 25 through channel 16 into channel 28. Sample gas containing the compounds to be measured, one of which is referred to as AB for brevity, is injected into the channel 28 where it is exposed to photons $h\gamma D$ resulting from the decay of D*. There is a net flow of carrier and sample gas through the detector chamber 12, as depicted in FIG. 2, from top to bottom. As mentioned previously this flow of gas exits the chamber 12 at the outlet 44.

Possible reactions that can be induced directly or indirectly by the source D* are:

$$D^* = D + h\gamma D \tag{1}$$

$$h\gamma D + AB = AB^+ + e^- + D \tag{2}$$

$$h\gamma D + AB = A + B^+ + e^- + D \tag{3}$$

$$h\gamma D + AB = AB^* + D \tag{4}$$

where $AB^* = AB + h\gamma$ $$h\gamma D + AB = A + B^* + D \tag{5}$$

where $B^* = B + h\gamma$ where $e-$ denotes a free electron, * denotes an excited state, $h\gamma D$ denotes photon emission from the excited dopant D*, and $h\gamma$ denotes spectral emission. The equations (4) and (5) describe reactions which form specific and characteristic emission spectra, thereby providing a characteristic signal which enables identification and quantification of the unknown sample compound AB. Spectral analysis can be performed using methods detailed in previously referenced U.S. Pat. No. 5,153,519. Equations (2) and (3) describe reactions which produce free electrons which are the basis of the preferred embodiment of this disclosure. The resulting electron population is measured with electrometer 36, with the measured electron current increasing with increasing concentration of a specific compound AB.

For purposes of detailed description of the operation, it will be assumed that the system comprises three ionization detectors. The first, second and third detectors utilize as carrier gasses helium, argon doped helium and krypton doped helium, respectively. Table 1 summarizes emission spectra from helium and spectra from argon and krypton doped helium. It should, however, be understood that other suitable carrier gas mixtures can be effectively used, and the data within Table 1 are presented primarily to support the example being presented.

TABLE 1

| EMISSION SPECTRA FROM HELIUM AND ARGON AND KRYPTON DOPED HELIUM | | |
|---|---|---|
| ACTIVE SPECIES | WAVELENGTH (nm) | ENERGY (eV) |
| He | 388 | |
| He$_2$ | 70–90 | 1.35—17.7 |
| Ar | 104.8 | 11.83 |
| Ar | 106.6 | 11.62 |
| Kr | 116.5 | 10.64 |
| Kr | 123.6 | 10.03 |
| Ar$_2$ | 121–133.6 | 9.28–10.24 |
| Kr$_2$ | 139.7–152.8 | 8.11–8.87 |

The sample gas is split and passed through detectors as previously described. The electrometer output current from the detector with helium as a carrier gas, $C_{He}$, is measured and stored within the computer 60. The electrometer outputs $C_{He+Ar}$ and $C_{He+Kr}$ from the second and third detectors, respectively, are measured simultaneously and likewise stored within the computer 60. The ratios $$R'_{Ar} = C_{He+Ar}/C_{He} \tag{6}$$

and $$R'_{Kr} = C_{He+Kr}/C_{He} \tag{7}$$

are next computed. As a precursor to analyzing samples containing unknown compounds, the system is first "calibrated" by measuring the ratios $R'_{Ar}$ and $R'_{Kr}$ using a calibration gas comprising a known amount of benzene. All other constituents of the calibration gas exhibit ionization potentials above the highest emission level of the carrier gas and, therefore, do not contribute to the electrometer current readings of the detectors. The ratios defined in equations (6) and (7) for the benzene calibration gas will be defined as $R''_{Ar}$ and $R''_{Kr}$, respectively. Ratios measured using the unknown sample, normalized to a corresponding reading for benzene of 100, are computed from the equations $$R_{Ar} = 100(R'_{Ar}/R''_{Ar}) \tag{8}$$

and $$R_{Kr} = 100(R'_{Kr}/R''_{Kr}) \tag{9}$$

Table 2 lists normalized ratios $R_{Kr}$ and $R_{Ar}$ which have been measured for selected compounds. The tabulation is by no means extensive and is presented for illustration purposes only. Assume that for an unknown sample gas, $R_{Ar}$ is measured to be 77.8+/−0.8, where the designated uncertainty is attributed to random errors in the system. Referring to Table 2, the compounds $C_3H_7NO_2$ ($R_{Ar}$=78.3) and $CH_3CHO$ ($R_{Ar}$=77.9) and 1-pentene ($R_{Ar}$=77.6) all fall within the uncertainty of the measured value of +/−0.8. If the system contained only two detectors, the unknown compound could not be uniquely identified, at least on the basis of the ionization detection measurements. Assume that $R_{Kr}$ is measured to be 37.4+/−0.4. Again referring to Table 2, it is apparent that only 1-pentene would yield values within the range of the measured values of $R_{Ar}$ and $R_{Kr}$ since the tabulated values of $R_{Kr}$ for $C_3H_7NO_2$ and $CH_3CHO$ are 0.74 and 43.4, respectively. The unknown compound is, therefore, identified as 1-pentene. The concentration of 1-pentene is obtained from the magnitude of either electrometer reading $C_{Ar}$ or $C_{Kr}$ using a predetermined calibration relationship obtained from $C_{Ar}$ or $C_{Kr}$ using a calibration sample gas containing known concentrations of 1-pentene.

Figure 4A:
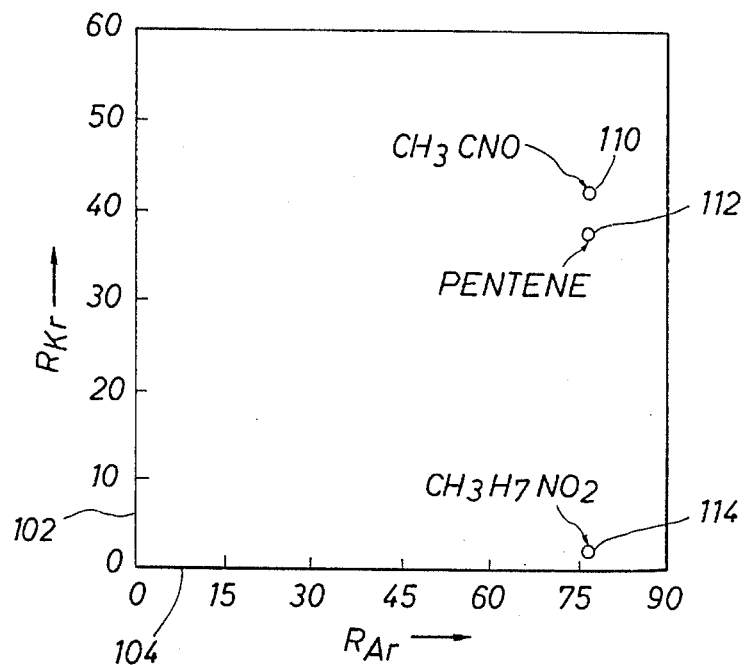
FIGS. 4A and 4B illustrate the compound identifications step of the data analysis procedure for a system comprising three and four detectors, respectively.

All computations and comparisons as outlined in the previous example are performed in real time with the computer 60. Results of the analyses are presented in a suitable format with the output device 38. The identification portion of the analysis is depicted graphically in FIG. 4A. $R_{Ar}$ is plotted on the axis denoted by the numeral 104 and $R_{Kr}$ is plotted on the axis denoted by the numeral 102. Corresponding "coordinates" for 1-pentene, $C_3H_7NO_2$ and $CH_3CHO$, with expected systematic uncertainties for each value, are taken from Table 2 and depicted as circles denoted by the numerals 112, 114 and 110, respectively. Should the measured values of $R_{Ar}$ and $R_{Kr}$ plot within any circle uncertainty of the example compounds, then the unknown compound is thereby identified. In the previously discussed example, the measured values of $R_{Ar}$ and $R_{Kr}$ plot within the circle denoted as 112 therefore the unknown compound is identified as 1-pentene.

TABLE 2

NORMALIZED RESPONSE RATIOS $R_{Ar}$ AND $R_{Kr}$ FOR SELECTED COMPOUNDS

| COMPOUND | $R_{Ar}$ | $R_{Kr}$ |
| --- | --- | --- |
| $CS_2$ | 204.0 | 38.3 |
| 1-hexane | 81.7 | 41.8 |
| $C_3H_7NO_2$ | 78.3 | 0.74 |
| $CH_3CHO$ | 77.9 | 43.4 |
| 1-pentene | 77.6 | 37.4 |
| 2-methyl-1-pentene | 76.0 | 35.3 |
| heptane | 76.0 | 4.58 |
| 1-butene | 70.5 | 24.3 |
| butane | 62.4 | 1.13 |
| n-$C_3H_7OH$ | 60.9 | 10.2 |

Figure 4B:
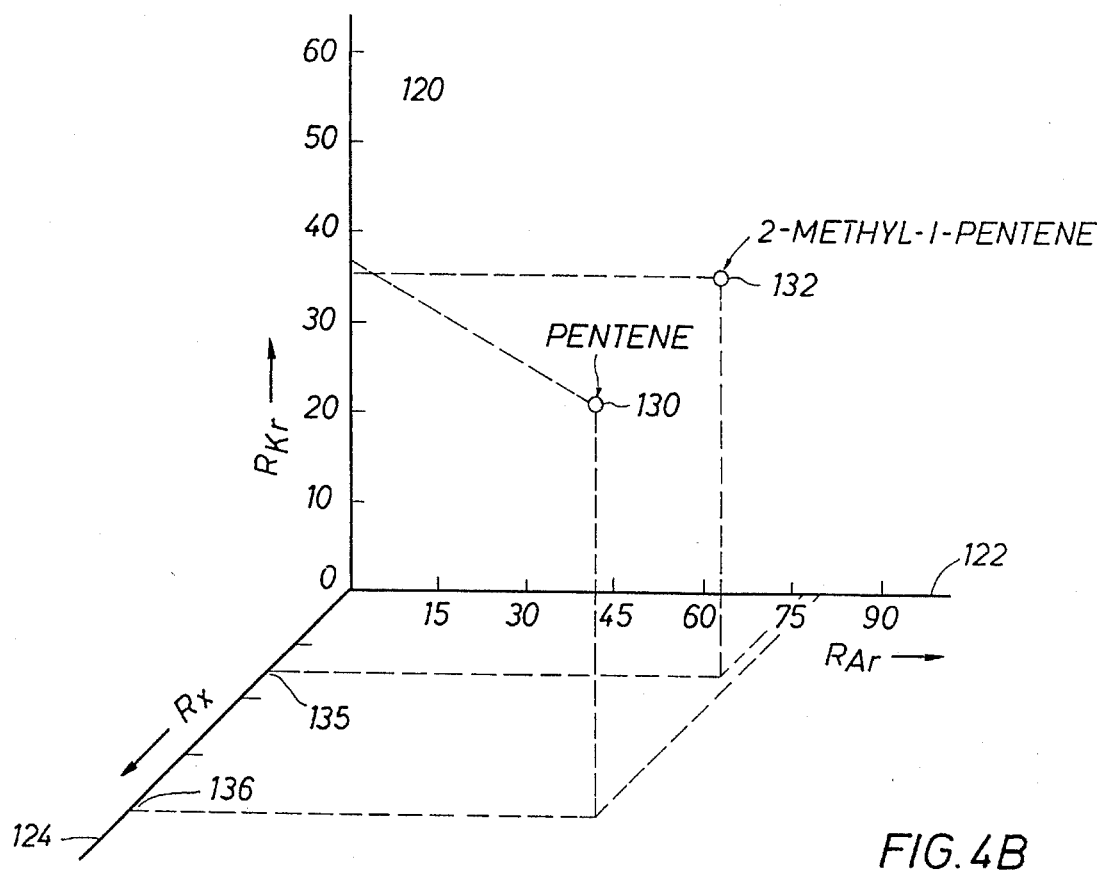

As a second example, assume that $R_{Ar}$ is measured to be 76.8+/−1.0 and $R_{Kr}$ is measured to be 36.0+/−2.0. The uncertainties of the measurements is much greater that usually encountered with the system, but are used for purposes of illustration. Referring again to Table 2, it is not possible to define uniquely the unknown compound as 1-pentene or 2-methyl-1-pentene since both fall within the uncertainty ranges of the measurements. This example illustrates the need for an additional detector with carrier gas dopant such that the normalized ratio from this detector, denoted as "$R_X$", will clearly delineate between the two compounds in question. The system using four detectors (which yields three ratios) is depicted graphically in FIG. 4B. Coordinates representing 1-pentene and 2-methyl-1-pentene, with spheres representing the systematic uncertainty of the system, are depicted as 132 and 130, respectively. $R_{Kr}$ and $R_{Ar}$ are plotted along the axes denoted by the numerals 120 and 122, respectively. The ratio from the additional detector, $R_X$, is plotted along the axis denoted by 124 and is in arbitrary units for purposes of illustration. Hypothetical values for $R_X$ for 1-pentene and 2-methyl-1-pentene, again used only for purposes of illustration, are denoted by the numerals 136 and 135, respectively. Should values of $R_{Ar}$, $R_{Kr}$ and $R_X$ measured for an unknown sample plot within the sphere of uncertainty for either compound, the unknown compound is thereby identified. The graphical interpretation is presented only for purposes of illustration. It should be understood that the graphical interpretation is easily adapted for computer interpretation within the computer 60 in the preferred embodiment of the invention.

In summary, the preferred embodiment of the disclosure is directed toward, although not limited to, the qualitative analysis of gas samples. A plurality of ionization detectors is used to analyze splits of the sample gas simultaneously. Constituents of the carrier gas are selected such that compounds to be measured are selectively ionized while other constituents of the sample gas are not ionized. This increases the signal-to-noise ratio of the measurement thereby maximizing accuracy and precision of the measurement.

While the foregoing disclosure is directed to the preferred embodiments of the present invention, other and further embodiments of the invention may be devised without departing from the basic scope thereof, and the scope thereof is determined by the claims which follow.

We claim:

1. A method for analyzing a sample gas comprising the steps of:
   (a) serially forming a plurality of carrier gases wherein at least one of said carrier gases comprises an inert gas and a dopant gas selected from a set of dopant gases;
   (b) flowing a current through said carrier gases;
   (c) energizing at least one component of said carrier gases to an excited state as a result of exposure to said current flow;
   (d) mixing a sample gas comprising one or more compounds with said energized carrier gases;
   (e) forming charged particles of said sample gas as a result of ionizing radiation emitted in the decay of said excited component of said carrier gases interacting with one or more compounds contained in said sample gas;
   (f) measuring the electrical currents resulting from the flow of said charged particles wherein said measurement step occurs after forming charged particles; and
   (g) selectively identifying one or more said compounds contained in said sample utilizing said current measurements.

2. The method of claim 1 further comprising the steps of:
   (a) providing a detector chamber for each of said plurality of carrier gases;
   (b) flowing each of said carrier gases through said provided detector chamber for exposure to said current flow;
   (c) energizing, within each said provided detector chamber, at least one component of each of said carrier gases to an excited state as a result of exposure to said current flow;
   (d) splitting said sample gas into portions thereby forming sample gas splits for flowing into each said provided detector chamber;
   (e) exposing said sample gas splits to said energized carrier gases within each said provided detector chamber;
   (f) forming charged particles within each said provided detector chamber as a result of ionizing radiation emitted in the decay of said excited components of said carrier gases interacting with one or more compounds contained within said sample gas splits;
   (g) measuring the electrical currents resulting from the flow of said charged particles within each said provided detector chamber thereby forming a set of electrical current measurements; and
   (h) identifying one or more compounds within said sample gas by utilizing said set of electrical current measurements and a predetermined relationship between said measured current set and the identity of said compounds.

3. The method of claim 2 wherein said dopants are selected such that the resonance energy of each of said dopant is different.

4. The method of claim 3 wherein said dopants are selected such that the resonance energy of at least one dopant is greater than the ionization energy of each said identified compounds within said sample gas.

5. The method of claim 4 wherein said electrical current measurements are made simultaneously within each of said provided detector chamber.

6. The method of claim 5 wherein said electrical current measurements are made during said current flows within each provided detector chamber.

7. The method of claim 5 wherein said electrical current measurements are made after the termination of said current flows within each provided detector chamber.

8. The method of claim 5 wherein said electrical current measurements are made in regions of said provided detector chambers remote from said current flow.

9. The method of claim 1 wherein the major constituent of said carrier gases is helium.

10. The method of claim 1 wherein said dopants are rare gases.

11. A gas detector for identifying compounds in a sample gas, comprising:

(a) a plurality of chambers with each chamber having a inlet at a first end and an outlet at a second end, and a gas flow path between said inlet and outlet;

(b) a source of carrier gas of a selected type for each said chamber;

(c) means for inserting said selected carrier gas into each said flow path of each said chamber;

(d) means for splitting a sample gas and flowing said sample gas splits into each of said chambers;

(e) two electrodes spaced apart and located to respond to current flow resulting in sparks within said each said chamber across said gas flow path and wherein the duration of said sparks minimizes electrode erosion and permits observation of phenomena occurring at and between said sparks and remote from said electrode location;

(f) means for measuring electrical currents resulting from ions which are produced by said sparks or by metastable species within said carrier gases interacting with said sample gas splits within each of said chambers; and (g) computing means for processing said measured electrical currents to identify selected compounds contained within said sample gas.

12. The apparatus of claim 11 wherein said means for measuring said electrical currents comprises, within each detector chamber, a collector and a bias electrode cooperating with an electrometer.

13. The apparatus of claim 11 wherein said means for flowing said sample gas splits into each of said detector chambers comprises an injection tube entering each chamber through a fitting on said second end of said chamber.

14. The apparatus of claim 11 wherein said computing means for processing said measured electrical currents to identify selected compounds contained within said sample gas further comprises a predetermined relationship between said measured electrical currents and the types of compounds yielding said measured electrical currents.

15. The apparatus of claim 11 wherein the major constituent of said carrier gases is helium.

16. The apparatus of claim 11 wherein minor constituents of said carrier gases comprise rare gases.

17. The apparatus of claim 11 wherein said the resonance energies of the minor constituents of said carrier gases are different.

18. The apparatus of claim 17 wherein the resonance energy of at least one constituent of at least one said carrier gas is greater than the ionization energy of each of said measured compound within said sample gas.

19. The apparatus of claim 11 further comprising means for recording said identified compounds.

20. A method for analyzing a sample gas comprising the steps of:

(a) forming first and second carrier gases each comprising a mixture of an inert gas and different dopant gases;

(b) flowing a current through said carrier gases;

(c) energizing at least one component of said carrier gases to an excited state as a result of exposure to said current flow;

(d) mixing a sample gas comprising one or more compounds with said energized carrier gases;

(e) forming charged particles of said sample gas as a result of ionizing radiation emitted in the decay of said excited component of said carrier gases interacting with one or more compounds contained in said sample gas;

(f) measuring the electrical currents resulting from the flow of said charged particles wherein said measurement step occurs in timed relationship to carrier gas flow; and (g) selectively identifying one or more said compounds contained in said sample utilizing said current measurements.

21. The method of claim 20 further comprising the steps of:

(a) providing a detector chamber for each of said carrier gases;

(b) flowing each of said carrier gases through said provided detector chamber for exposure to current flow therein;

(c) energizing, within each said provided detector chamber, at least one component of each of said carrier gases to an excited state as a result of exposure to said current flow;

(d) splitting said sample gas into portions thereby forming sample gas splits for flowing into each said provided detector chamber;

(e) exposing said sample gas splits to said energized carrier gases within each said provided detector chamber;

(f) forming charged particles within each said provided detector chamber as a result of ionizing radiation emitted in the decay of said excited components of said carrier gases interacting with one or more compounds contained within said sample gas splits;

(g) measuring the electrical currents resulting from the flow of said charged particles within each said provided detector chamber thereby forming a set of electrical current measurements; and (h) identifying one or more compounds within said sample gas by utilizing said set of electrical current measurements and a predetermined relationship between said measured current set and the identity of said compounds.

22. The method of claim 20 wherein said dopants are selected such that the resonance energy of each said dopant is different.

23. The method of claim 20 wherein said dopants are selected such that the resonance energy of at least one dopant is greater than the ionization energy of each said identified compounds within said sample gas.

* * * * *